United States Patent
Matsubara et al.

(10) Patent No.: US 6,230,544 B1
(45) Date of Patent: May 15, 2001

(54) FRICTIONAL WEAR TESTING APPARATUS AND FRICTIONAL WEAR TESTING METHOD

(75) Inventors: Tooru Matsubara; Minoru Tanaka, both of Nagaoka (JP)

(73) Assignee: Maocho Co., Ltd., Nigata (JP)

( * ) Notice: Subject to any disclaimer, the term of this patent is extended or adjusted under 35 U.S.C. 154(b) by 0 days.

(21) Appl. No.: 09/227,917

(22) Filed: Jan. 8, 1999

(30) Foreign Application Priority Data

| Apr. 8, 1998 | (JP) | 10-095963 |
| Sep. 30, 1998 | (JP) | 10-277423 |
| Dec. 14, 1998 | (JP) | 10-354530 |

(51) Int. Cl.$^7$ .................................................. G01N 3/56
(52) U.S. Cl. .................................................................. 73/7
(58) Field of Search ................................. 73/7, 8, 865.6, 73/9

(56) References Cited

U.S. PATENT DOCUMENTS

| 2,907,200 | * | 10/1959 | Roberts et al. | 73/7 |
| 3,229,498 | * | 1/1966 | Oakes | 73/7 |
| 3,592,362 | * | 7/1971 | Kane | 73/7 |
| 4,442,707 | * | 4/1984 | Tuzson | 73/7 |

FOREIGN PATENT DOCUMENTS

| 4020146 | * | 1/1992 | (DE) . |  |
| 2-24335 |  | 5/1990 | (JP) | G01N/3/56 |
| 48745 | * | 2/1992 | (JP) . |  |
| 558107 | * | 6/1977 | (RU) . |  |
| 1388762 | * | 4/1988 | (SU) . |  |
| 1608480 | * | 11/1990 | (SU) . |  |
| 1663504 | * | 7/1991 | (SU) . |  |

* cited by examiner

*Primary Examiner*—Hezron Williams
*Assistant Examiner*—Nashmiya Fayyaz
(74) *Attorney, Agent, or Firm*—Sughrue, Mion, Zinn, Macpeak & Seas, PLLC

(57) ABSTRACT

To provide a very novel frictional wear testing apparatus and a frictional wear testing method by which injection material injected to a test piece is not dispersed, the frictional wear characteristics may be measured for a short period time in very simplified steps, a measurement error is suppressed with a good reproduceability and it is possible to make the apparatus small in size. The frictional wear testing apparatus for measuring anti-wear characteristics of a test piece such as a metal member or a ceramic member, includes a fixing mechanism for fixing the test piece and an injection mechanism for reducing a mass of the test piece by injecting injection material, in which grinding particles are mixed into liquid, to the test piece fixed to the fixing mechanism together with pressurized air.

13 Claims, 3 Drawing Sheets

FRICTIONAL WEAR TESTING APPARATUS AND FRICTIONAL WEAR TESTING METHOD

BACKGROUND OF THE INVENTION

The present invention relates to a frictional wear testing apparatus and frictional wear testing method for measuring wear resistance (anti-abrasion) characteristics of metal material or ceramic material.

Since ceramics are very hard, in the case where the evaluation of the wear resistance characteristics is performed in a general frictional wear testing method such as a pinion disc method or an abrasion testing method, the wear is hardly, developed. As a result, the measurement takes a long time and the measurement error is also remarkable. Then, in order to solve this problem, an erosion frictional wear test is proposed as a frictional wear testing method.

In this erosion frictional wear test, injection material containing grinding particles in an accelerated gas flow is injected onto a test piece such as a ceramic member for a constant period of time, and the mass reduction or the frictional worn volume of the test piece is measured for the evaluation. This is a very simple method because a size of the test piece to be used is such as a bending strength test piece defined by JIS (Japanese Industrial Standards), for example. In addition, the test is superior in produceability of data. Thus, the test has excellent features in comparison with the general frictional wear tests.

However, in the method such as an erosion frictional wear test using the injection material which is obtained by mixing air and grinding particles, since the grinding particles and the cutting debris of the test piece is likely to fly and drift in the air, it is necessary to enhance air-tight property of an injection chamber in order to prevent the grinding particles or the like from leaking to the outside of the injection chamber. Also, it is necessary to provide a device such as a dust collection filter or a cyclone for collecting the particles or the like. The overall apparatus is large in size and complicated in construction, resulting in increased cost.

Also, since the particles drift for a while after the injection material has been injected, if the injection chamber is opened to pick up the test piece immediately after the completion of the test, there is a fear that the particles would be dispersed to the outside. Accordingly, in the case where the test piece is picked up after the completion of the test, one has to wait until the grinding particles drifting in the injection chamber are completely removed. Therefore, it takes a long time for one measurement.

Also, in the method for mixing the grinding particles into the accelerated air flow, the collision force by which the grinding particles are collided against the test piece depends upon the humidity. In addition, the higher the humidity, the more the error will become. It is necessary to set the humidity at a constant level for every measurement within the injection chamber in order to suppress the measurement error. Accordingly, the conventional method suffers from a problem that the testing operation is very complicated and troublesome.

SUMMARY OF THE INVENTION

In view of the above-noted defects, an object of the present invention is to provide a very novel frictional wear testing apparatus and a frictional wear testing method by which injection material injected to a test piece is not dispersed, the frictional wear characteristics may be measured for a short period time in very simplified steps, a measurement error is suppressed with a good reproduceability and it is possible to make the apparatus small in size.

In order to attain this and other objects, according to a first aspect of the present invention, there is provided a frictional wear testing apparatus for measuring anti-wear characteristics of a test piece such as a metal member or a ceramic member, comprising a fixing mechanism for fixing the test piece and an injection mechanism for reducing a mass of the test piece by injecting injection material, in which grinding particles are mixed into liquid, to the test piece fixed to the fixing mechanism together with pressurized air.

In the frictional wear testing apparatus according to the first aspect, according to a second aspect of the invention, particles which have been mixed into the injection material are one selected from the group consisting of resin particles, metal particles, ceramic particles and glass particles having a particle size of several microns to several hundreds microns, and liquid is one selected from the group consisting of water, aqueous solution such as alkaline solution and alcohol solutions.

Also, in the frictional wear testing apparatus according to the first aspect of the invention, according to a third aspect of the invention, the fixing mechanism comprises a rotational mechanism which may adjust a contact angle between the injection material and the test piece by rotating the test piece fixed to the fixing mechanism.

Also, in the frictional wear testing apparatus according to the second aspect of the present invention, according to a fourth aspect of the invention, the fixing mechanism comprises a rotational mechanism which may adjust a contact angle between the injection material and the test piece by rotating the test piece fixed to the fixing mechanism.

Also, in the frictional wear testing apparatus according to the third aspect of the invention, according to a fifth aspect of the invention, the rotational mechanism is set so that an injection travel distance of the injection material injected to the test piece is kept constant even if the test piece is rotated.

Also, in the frictional wear testing apparatus according to the fourth aspect of the invention, according to a sixth aspect of the invention, the rotational mechanism is set so that an injection travel distance of the injection material injected to the test piece is kept constant even if the test piece is rotated.

Also, in the frictional wear testing apparatus according to any one of the preceding aspects 1 to 6, according to a seventh aspect of the invention, a collection mechanism for collecting the injection material injected from the injection mechanism to the test piece is provided below the test piece fixed to the fixing mechanism, the collection mechanism and the injection mechanism are connected to each other by a flow delivery mechanism for delivering the injection material, and the injection material injected to the test piece is again injected from the injection mechanism to the test piece through the collection mechanism and the flow delivery mechanism.

Also, in the frictional wear testing apparatus according to the seventh aspect of the invention, according to an eighth aspect of the invention, the collection mechanism comprises an agitating mechanism for mixing the grinding particles and the liquid of the injection material within the collection mechanism substantially at a constant ratio and in a uniform manner.

Also, according to a ninth aspect of the invention, there is provided a frictional wear testing apparatus for measuring anti-wear characteristics of a test piece such as a metal member or a ceramic member, comprising a fixing mechanism for fixing the test piece and an injection mechanism for reducing a mass of the test piece by injecting injection material to the test piece fixed to the fixing mechanism together with pressurized air, the injection material is obtained by mixing grinding particles, which are one selected from the group consisting of resin particles, metal particles, ceramic particles and glass particles having a particle size of several microns to several hundreds microns, into solutions, which are one selected from the group consisting of water, aqueous solution such as alkaline solution and alcohol solutions, the fixing mechanism comprises a rotational mechanism which may adjust a contact angle between the injection material and the test piece by rotating the test piece fixed to the fixing mechanism, the rotational mechanism is set so that the test piece fixed to the fixing mechanism is located on an axis of rotational mechanism to keep an injection travel distance of the injection material injected to the test piece constant even if the test piece is rotated, a collection mechanism for collecting the injection material injected from the injection mechanism to the test piece is provided below the test piece fixed to the fixing mechanism, the collection mechanism comprises an agitating mechanism for mixing the grinding particles and the liquid of the injection material within the collection mechanism substantially at a constant ratio and in a uniform manner, the collection mechanism and the injection mechanism are connected to each other by a flow delivery mechanism for delivering the injection material, and the injection material injected to the test piece is again injected from the injection mechanism to the test piece through the collection mechanism and the flow delivery mechanism together with pressurized air, and wherein a pressure adjusting mechanism is provided for adjusting the injection pressure of the injection material and the pressurized air.

Also, in a frictional wear testing method, a test piece is reduced in mass and the loss of the test piece and the cut shape thereof are measured by using the frictional wear testing apparatus according to any one of the first to the sixth and ninth aspects of the invention, for measuring antiwear characteristics of the test piece.

Also, in the frictional wear testing method, a test piece is reduced in mass and the loss of the test piece and the cut shape thereof are measured by using the frictional wear testing apparatus according to the eighth aspect of the invention, for measuring anti-wear characteristics of the test piece.

The injection material is injected at a high speed together with the compressed air and collided with the test piece so that the test piece is lost the weight.

In this case, since the injection material injected to the test piece is made by mixing the grinding particles into the liquid, the injection material injected at a high speed fall in drops of liquid containing grinding particles immediately after the collision with the test piece. Accordingly, the grinding particles and the cut debris of the test piece are remained in the drop of liquid, so that the grinding particles and the cut debris will not be dispersed in the air. The injection material may be easy to collect. The frictional wear testing machine may be operated with extreme ease.

Also, it is possible to wear the test piece by friction for a very short period of time by injecting the injection material, which are mixture of liquid and the grinding particles, to the test piece together with the compressed air. In addition, it may not suffer a damp, so that it is easy to control the machine. The errors in measurement are small and the frictional wear test is performed with a good reproduceability.

Since the invention is thus constructed, it is easy to measure the frictional wear characteristics in a short period of time in the very simple process order without dispersing the injection material injected to the test piece. Errors in measurement are very small and the apparatus is excellent in reproduceability. It is possible to provide a very epoachmaking frictional wear testing apparatus and method which may be readily miniaturized.

DESCRIPTION OF THE PREFERRED EMBODIMENTS

Figure 1:
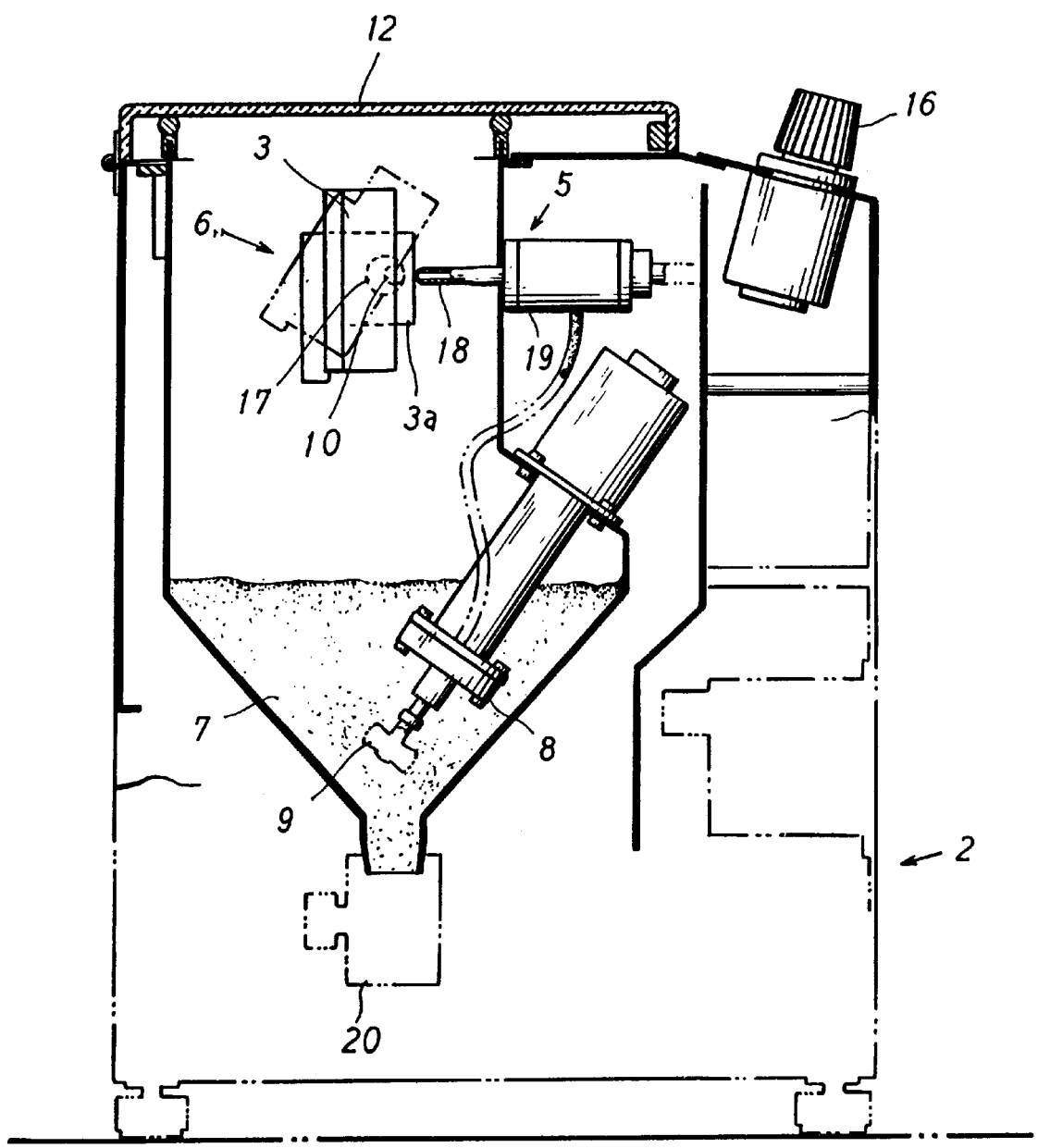
FIG. 1 is a side elevational cross-sectional view in accordance with an embodiment of the present invention.
Figure 2:
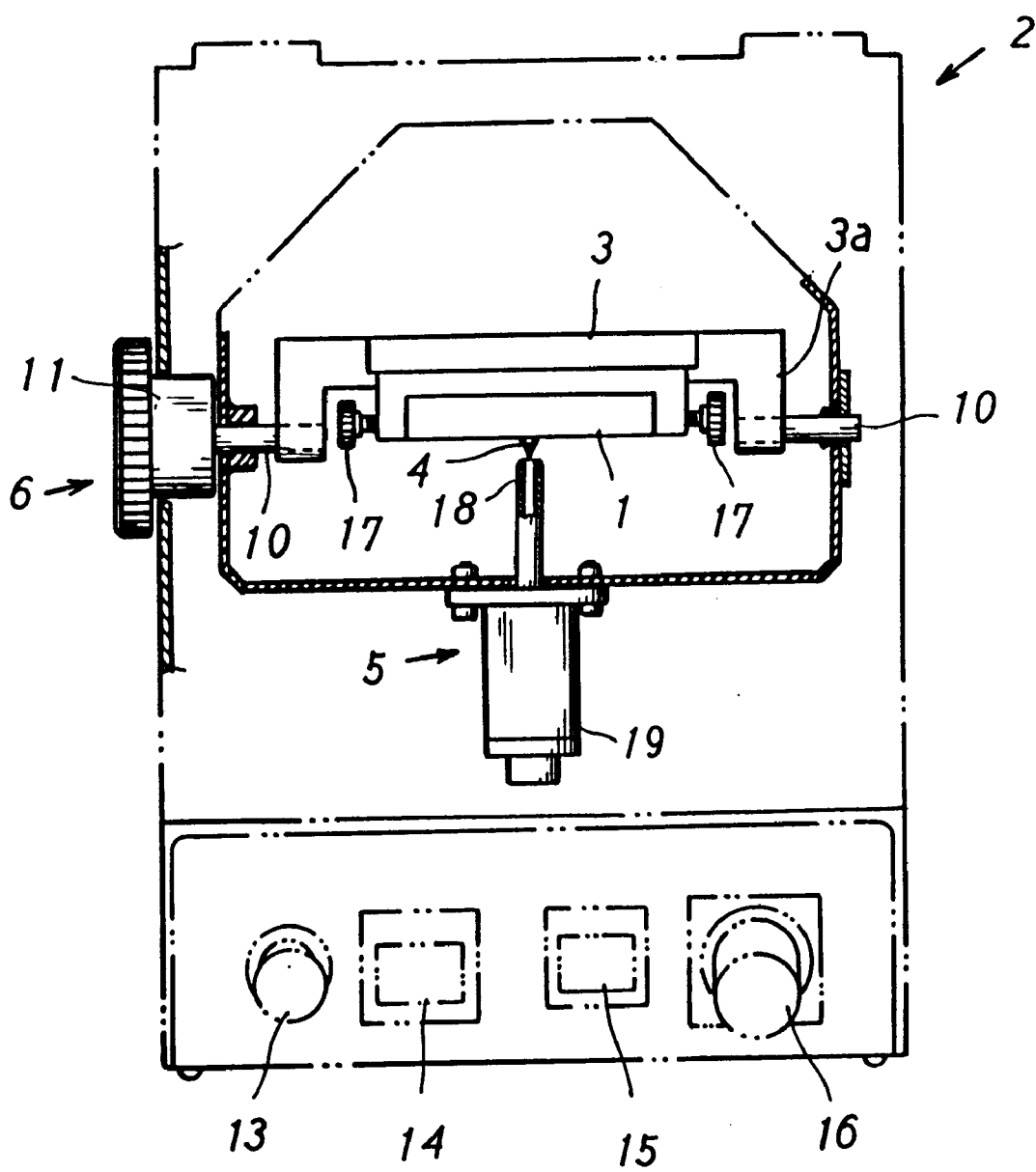
FIG. 2 is a plan cross-sectional view in according with the embodiment of the invention.

One embodiment of the present invention will now be described with reference to the accompanying drawings.

According to the embodiment, a frictional wear testing machine 2 is provided for measuring the wear resistance characteristics of a test piece 1 made of hard material such as metal or ceramics. The testing machine 2 has a fixing mechanism 3 for fixing the test piece 1 and an injection mechanism 5 for cutting the test piece 1 by injecting injection material 4 to the test piece 1 fixed to the fixing mechanism 3. The injection material 4 is made by mixing grinding particles into liquid.

The grinding particles mixed into the injection material 4 have a diameter of several microns to several hundreds of microns and are made of fine particles such as resin, metal, ceramics or glass. The injection material 4 is made by dispersing the grinding particles to water to form slurry. Also, in addition to use of water, in compliance with the purpose, for example, aqueous solution such as alkaline liquid may be used for degreasing. Also, it is possible to use solution such as alcoholic liquid.

The injection mechanism 5 is composed of an injection nozzle 18 for injecting the injection material 4 and a mixing chamber 19 for injecting the injection material 4 from the injection nozzle 18 together with the compressed air.

A fastening member 17 is provided in the fixing mechanism 3 so that both end portions of the test piece 1 are fastened and fixed by the fastening member 17.

Also, a rotational mechanism 6 is provided to the fixing mechanism 3. A rotary shaft 10 is provided at both end portions of the fixing mechanism 3 for rotating the fastening member 17. An angle of the surface of the test piece 1 facing the injection material 4 may be changed relative to the injection material 4 injected from the injection mechanism 5 when the rotary shaft 10 is rotated by operating a rotary knob 11 provided in a suitable position of the frictional wear testing machine 2.

Also, in the rotational mechanism 6, the rotary shaft 10 for rotating the fixing mechanism 3 and the surface, to be tested, of the test piece 1 fixed to the fixing mechanism 3 are located substantially on the same line. An injection travel distance of the injection material 4 injected to the test piece 1 is kept constant even if the test piece 1 is rotated. Incidentally, in the drawings, reference character 3a denotes projecting portions provided on the right and left sides of the fixing mechanism 3. The fixing mechanism 3 and the rotary shaft 10 are formed integrally with each other at the projecting portions 3a so that the injection travel distance of the injection material 4 to be injected to the test piece 1 is kept constant when the test piece 1 is rotated.

A collection mechanism 7 for collecting the injection material 4 colliding the test piece 1 and dropping downwardly is provided below the test piece 1 fixed to the fixing mechanism 3.

The collection mechanism 7 is formed into a water bath having a downwardly tapered shape so that the injection material 4 injected and dropping downwardly from the injection mechanism 5 may be stagnant and collected therein. A flow delivery mechanism 8 in communication with the injection mechanism 5 is provided in the collection mechanism 7 so that the injection material 4 injected from the injection mechanism 5 is recirculated in the apparatus.

Also, an agitating mechanism 9 composed of agitating blades is provided in the collection mechanism 7 so that the injection material 4 stagnant in the collection mechanism 7 is agitated and the water and the grinding particles of the injection material 4 are kept uniformly in the dispersed condition having a constant concentration distribution.

Also, a discharge portion 20 for discharging the injection material 4 when the injection material 4 is contaminated by the grinding particles or the like is provided at the lowermost position of the collection mechanism 7.

Reference numeral 12 denotes a resin-made transparent cover member for preventing the injection material 4 from being dispersed to the outside (since the cover member 12 is transparent, the state of each part within the apparatus may be seen well). Numeral 13 denotes a start button for injecting the injection material 4. Numeral 14 denotes a timer, numeral 15 denotes a pressure meter, numeral 16 denotes a pressure adjusting portion for adjusting a pressure of the compressed air for injecting the injection material 4 from the injection nozzle 18.

The operation of the embodiment will now be described.

The test piece 1 is machined in advance into a predetermined shape (that may be attached to or detached from the fixing mechanism 3). The mass (W1) of the test piece 1 is measured.

On the other hand, a predetermined amount of water and grinding particles are introduced as the injection material 4 into the water bath that is the collection mechanism 7 by opening the cover member 12 of the frictional wear testing machine 2.

Subsequently, the cover member 12 is closed and the timer 14 is set at a suitable time. The start button 13 is operated so that the injection material 4 is injected from the injection mechanism 5 together with the pressurized air. Also, in this case, the injection material 4 is agitated by the agitating mechanism 9 in the collection mechanism 7.

Subsequently, one waits until the injection of the injection material 4 is stabilized. The pressure adjusting portion 16 is operated so that the injection pressure is adjusted at a predetermined level. Also, the injected injection material 4 is collected and the concentration of the injection material 4 is measured. It is confirmed whether or not the injection material 4 injected from the injection nozzle 18 has the predetermined concentration (grinding particles/water).

Subsequently, the start button 13 is operated to stop the injection.

Subsequently, the cover member 12 is opened and the test piece 1 is fixed to the fixing mechanism 3.

Subsequently, the cover member 12 is closed and the timer 14 is set at a predetermined injection time. After it is confirmed that the concentration of the injection material 4 is kept constant by the agitating mechanism 9, the start button 13 is operated to start the test.

In the test, the injection material 4 and the pressurized air are injected together toward the test piece 1 from the injection mechanism 5. The surface of the test piece 1 is abraded at a high speed by the synergetic effect of the water, the grinding particles and the pressurized air in a predetermined time to lose the weight. Also, the injection material 4 is injected from the injection mechanism 5 and collides against the test piece 1 to cut a part of the test piece and to drop to the collection mechanism 7. The water and the grinding particles which constitute the injection material 4 are agitated by the agitating mechanism 9 within the collection mechanism 7 so that the grinding particles are kept from precipitating on the lower portion of the collecting mechanism 7 and a uniform and predetermined rated concentration. Also, the injection material 4 is delivered again to the injection mechanism 5 by the flow delivery mechanism 8 provided in the collection mechanism 7 to be recirculated within the apparatus.

When a predetermined time has lapsed and the injection of the injection material 4 has been finished, the cover member 12 is to be opened and the test piece 1 is picked up. The injection material 4 adhered to the test piece 1 is washed and the test piece 1 is dried.

The mass (W2) of the test piece 1 after the injection is measured and the loss of the mass (W1–W2) is obtained. Thus, the frictional wear amount and the frictional wear resistance characteristics are evaluated by the loss of the mass. Also, it is preferable to evaluate the cut shape of the test piece 1.

Figure 3:
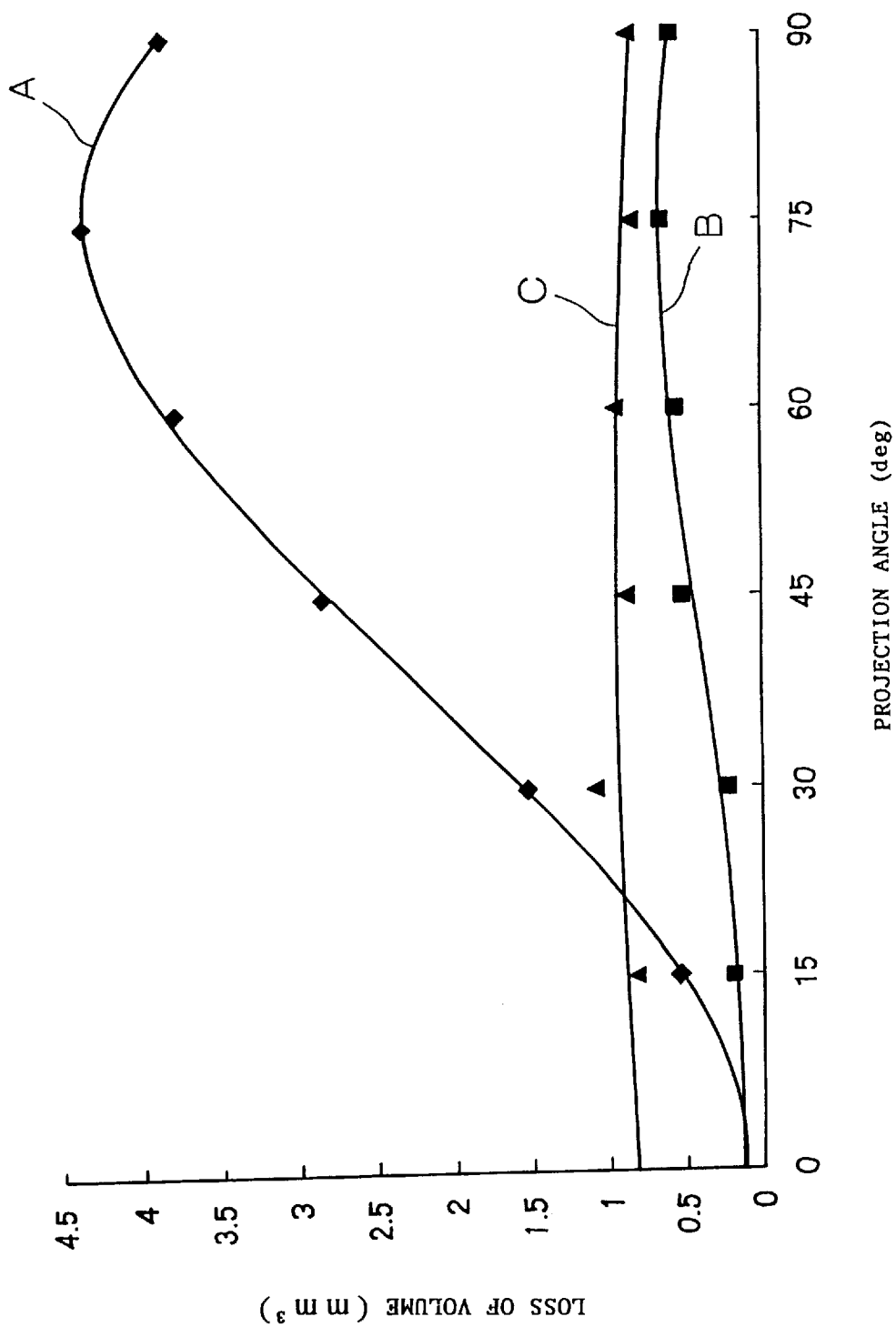
FIG. 3 is a graph showing the difference between the present invention and the conventional methods.

FIG. 3 shows results of three-minute frictional wear test for each test piece 1 by using the frictional wear testing machine 2 in accordance with the foregoing embodiment. Alumina ($Al_2O_3$: A in FIG. 3), silicon nitride ($Si_3N_4$: B in FIG. 3), and carbon tool steel (SK5(H): C in FIG. 3) were used for the test piece 1 (sample). Also, in the injection material 4, Alumina (having a particle size: 63 to 125 $\mu$m) was used for the grinding particles, the water was used for the liquid, and it had the the volume ratio of grinding particles:liquid=20:80 and the injection pressure of 2 $kg/cm^2$.

Thus, in comparison with the tests in accordance with the pinion disc method or the abrasion disc method, the mass of each test piece 1 was reduced well in accordance with the very short period of time for the test, i.e., the three-minute test. It was confirmed that the good anti-wear evaluation might be performed for the test piece 1 in for a short period of time even with respect to the very hard material such as alumina that is a kind of ceramics.

It is also confirmed that the frictional wear characteristics (angle dependency) characterized by the material for each test piece 1 might be simple and clear by performing the test by changing the projection angle of the injection material 4 relative to the surface of the test piece 1 by the rotational mechanism 6. Namely, by collecting a number of such sampling data, the judgement of the frictional wear characteristics for each material may readily be performed in comparison with the collected frictional wear test data. In addition, even if a material of test piece is uncertain, it is possible to identify the material by measuring the frictional wear characteristic thereof.

Also, the repeated frictional wear tests were conducted for the same sample. The numerical errors were small relative to the predicted mass reduction. Also, the cut condition of the test piece 1 was kept constant. Thus, it was confirmed that according to this embodiment, the frictional wear test is performed with a good reproduceability.

The advantage of the embodiment will be described.

Since the grinding particles or the cut debris may be well removed away from the test piece 1 by the liquid in the injection material 4, the injection material 4 injected from the injection mechanism 5 is always brought into contact with the test piece 1. The mass reduction of the test piece 1 may be developed stably and in a good condition.

Since the heat generated when the test piece 1 is cut by the liquid contained in the injection material 4 may be removed well, the test piece 1 is cut at a temperature under a constant condition and the mass is lost.

Also, since the film of the liquid is formed in the grinding particles contained in the injection material 4, the surface area of the grinding particles is increased and the loss of the injection pressure is small.

Since the liquid and the grinding particles contained in the injection material 4 become particles due to an expansion of compressed air and are brought into contact with the test piece 1, it is possible to exhibit a high cutting force with a low injection power in comparison with the conventional erosion friction wear test.

As described above, in accordance with the embodiment, it is possible to reduce the mass of the very hard material such as ceramics in a very short period of time, and it is moreover possible to perform the frictional test with a good reproduceability without a remarkable measurement error.

Since the embodiment is constituted as described above, it is possible to measure the frictional wear characteristics in a very short period time for the very hard material such as ceramics in the very simple process order. Also, it is possible to provide a frictional wear testing machine that is very simple and excellent in reproduceability without any large measurement error.

Also, since the injection material 4 injected drops immediately after the collision with the test piece 1, the grinding particles and the cut debris which are fine particles will not be dispersed for a long period of time in the air. It is unnecessary to mount a collection filter or a cyclone for collecting the grinding particles or to enhance the sealability of the injection chamber into which the injection material is to be injected as in the conventional frictional wear testing machine. It is possible to provide a frictional wear testing machine that is excellent in practical use and which may readily be miniaturized.

Also, since the water drop containing the grinding particles is stagnant in the collection mechanism 7 provided below the test piece 1 fixed to the fixing mechanism 3 and the injection material 4 is again injected from the injection mechanism 5 by the flow delivery mechanism 8 for communicating the collection mechanism 7 and the injection mechanism 5 with each other, the injection material container or the collection container is dispensed with and the apparatus may be small in size. It is thus possible to provide a frictional wear testing machine that is more excellent in practical use because the injection material 4 may be used in a recycling manner.

Also, since the agitating mechanism 9 is provided in the collection mechanism 7, the grinding particles contained in the injection material 4 are dispersed uniformly. At all the time, the injection material 4 is delivered to the injection mechanism 5 at a constant concentration, and there is no error caused by the non-uniformity of the grinding material concentration. In addition, it is possible to provide a frictional wear testing machine that is further excellent and in which the nozzle of the injection mechanism 5 or the flow delivery mechanism 8 is hardly clogged.

Also, since the rotational mechanism 6 is provided in the fixing mechanism 3, it is possible to provide a frictional wear testing machine that is further excellent in practical use by more exactly knowing the frictional wear characteristics of the test piece 1 by performing the tests by changing the angle of the surface of the test piece 1 relative to the injection material 4 injected.

Also, since the injection travel distance of the injection material 4 injected to the test piece 1 is kept constant even if the test piece 1 is rotated by the rotational mechanism 6, it is possible to readily perform the comparison of the evaluation even if the measurement is performed at a variety of angles. It is thus possible to provide the frictional wear testing machine that is further excellent in practical use.

Various details of the invention may be changed without departing from its spirit or its scope. Furthermore, the foregoing description of the embodiments according to the present invention is provided for the purpose of illustration only, and not for the purpose of limiting the invention as defined by the appended claims and their equivalents.

What is claimed is:

1. A frictional wear testing apparatus for measuring anti-wear characteristics of a test piece, comprising a fixing mechanism for fixing the test piece and an injection mechanism for reducing a mass of the test piece by injecting, together with pressurized air, injection material, in which grinding particles are mixed into solution with liquid, to the test piece fixed to said fixing mechanism.

2. The frictional wear testing apparatus according to claim 1, wherein the particles which have been mixed into the injection material are selected from the group consisting of resin particles, metal particles, ceramic particles and glass particles having a particle size of several microns to several hundreds microns, and the liquid is one selected from the group consisting of water, aqueous solution, alkaline solution, and alcohol solutions.

3. The frictional wear testing apparatus according to claim 1, wherein said fixing mechanism comprises a rotational mechanism which may adjust a contact angle between the injection material and the test piece by rotating the test piece fixed to said fixing mechanism.

4. The frictional wear testing apparatus according to claim 2, wherein said fixing mechanism comprises a rotational mechanism which may adjust a contact angle between the injection material and the test piece by rotating the test piece fixed to said fixing mechanism.

5. The frictional wear testing apparatus according to claim 3, wherein said rotational mechanism is set so that an injection travel distance of the injection material injected to the test piece is kept constant even if the test piece is rotated.

6. The frictional wear testing apparatus according to claim 4, wherein said rotational mechanism is set so that an injection travel distance of the injection material injected to the test piece is kept constant even if the test piece is rotated.

7. The frictional wear testing apparatus according to any one of claims 1 to 6, wherein a collection mechanism for collecting the injection material injected from said injection mechanism to the test piece is provided below the test piece fixed to said fixing mechanism, said collection mechanism and said injection mechanism are connected to each other by a flow delivery mechanism for delivering the injection material, and the injection material injected to the test piece is again injected from said injection mechanism to the test piece through said collection mechanism and said flow delivery mechanism.

8. The frictional wear testing apparatus according to claim 1, wherein a collection mechanism for collecting the injection material injected from said injection mechanism to the test piece is provided below the test piece fixed to said fixing mechanism, said collection mechanism and said injection mechanism are connected to each other by a flow delivery mechanism for delivering the injection material, and the injection material injected to the test piece is again injected from said injection mechanism to the test piece through said collection mechanism and said flow delivery mechanism, and wherein said collection mechanism comprises an agitating mechanism for mixing the grinding particles and the liquid of the injection material within said collection mechanism substantially at a constant ratio and in a uniform manner.

9. A frictional wear testing apparatus for measuring anti-wear characteristics of a test piece, comprising:

a fixing mechanism for fixing the test piece;

an injection mechanism for reducing a mass of the test piece by injecting, together with pressurized air, injection material to the test piece fixed to said fixing mechanism, said injection material is obtained by mixing grinding particles, which are selected from the group consisting of resin particles, metal particles, ceramic particles and glass particles having a particle size of several microns to several hundreds microns, into solutions, which are selected from the group consisting of water, aqueous solution, alkaline solution, and alcohol solutions;

said fixing mechanism comprising a rotational mechanism having a rotary shaft which may adjust a contact angle between the injection material and the test piece by rotating the test piece fixed to said fixing mechanism, said rotational mechanism set so that the test piece fixed to the fixing mechanism is located on an axis of rotation of the rotational mechanism to keep an injection travel distance of the injection material injected to the test piece constant even if the test piece is rotated;

a collection mechanism for collecting the injection material injected from said injection mechanism to the test piece provided below the test piece fixed to said fixing mechanism, said collection mechanism comprising an agitating mechanism for mixing the grinding particles and the liquid of the injection material within said collection mechanism substantially at a constant ratio and in a uniform manner, said collection mechanism and said injection mechanism connected to each other by a flow delivery mechanism for delivering the injection material, and wherein the injection material injected to the test piece is again injected from said injection mechanism to the test piece through said collection mechanism and said flow delivery mechanism together with pressurized air; and a pressure adjusting mechanism provided for adjusting the injection pressure of the injection material and the pressurized air.

10. A friction wear testing method wherein a test piece is reduced in mass and the loss of the test piece and the cut shape thereof are measured by using the frictional wear testing apparatus according to any one of claims 1 to 6 or 9, for measuring anti-wear characteristics of the test piece.

11. A frictional wear testing method wherein a test piece is reduced in mass and the loss of the test piece and the cut shape thereof are measured by using the frictional wear testing apparatus according to claim 8, for measuring anti-wear characteristics of the test piece.

12. The frictional wear testing method according to claim 10, wherein said injection material contains grinding particles and liquid in a ratio of 20:80.

13. The frictional wear testing method according to claim 11, wherein said injection material contains grinding particles and liquid in a ratio of 20:80.

* * * * *

UNITED STATES PATENT AND TRADEMARK OFFICE
CERTIFICATE OF CORRECTION

PATENT NO.    : 6,230,544 B1
DATED         : May 15, 2001
INVENTOR(S)   : Tooru Matsubara and Minoru Tanaka It is certified that error appears in the above-identified patent and that said Letters Patent is hereby corrected as shown below:

<u>Title page,</u>
Item [73], should read:

-- [73] Assignee: Macoho Co., Ltd., Niigata (JP);

<u>Column 6,</u>
Line 49, delete "for" (second occurrence)

Signed and Sealed this

Fourteenth Day of January, 2003

JAMES E. ROGAN
*Director of the United States Patent and Trademark Office*